United States Patent [19]

Jesse et al.

[11] Patent Number: 5,104,991
[45] Date of Patent: Apr. 14, 1992

[54] PREPARATION OF PHENYLOXADIAZOLYLANILINES

[75] Inventors: Joachim Jesse, Weisenheim; Hartmut Kanter, Ludwigshafen, both of Fed. Rep. of Germany

[73] Assignee: BASF Aktiengesellschaft, Ludwigshafen, Fed. Rep. of Germany

[21] Appl. No.: 473,409

[22] Filed: Feb. 1, 1990

[30] Foreign Application Priority Data

Feb. 21, 1989 [DE] Fed. Rep. of Germany ........ 3905242

[51] Int. Cl.$^5$ ............................................ C07D 271/06
[52] U.S. Cl. .................................................... 548/131
[58] Field of Search ........................................ 548/131

[56] References Cited

FOREIGN PATENT DOCUMENTS 2101559 7/1972 Fed. Rep. of Germany .
2457687 10/1975 Fed. Rep. of Germany .

OTHER PUBLICATIONS

Chemical Pharmaceutical Bulletin, Band 23, Nr. 12, Dec. 1974, Seiten 3178–3183, Tokyo, JP: K. Nagahara et al.: "Sur la formation d'Oxadiazoles-1,2,4 par action de benzamidoximes sur des anhydrides isatoiques" *Insgesam t* .
Ullmanns Encyklopadie Der Technischen Chemie, 4th edition, vol 22, pp. 468–488.
Schwartz Surface Active Agents vol. I, p. 513 (1949).

*Primary Examiner*—Robert Gerstl
*Attorney, Agent, or Firm*—Oblon, Spivak, McClelland, Maier & Neustadt

[57] ABSTRACT

Phenyloxadiazolylanilines are prepared by reaction of a benzonitrile in an aqueous reaction medium first with hydroxylamine or an acid addition salt thereof to give a benzamideoxime and then with an isatoic anhydride to give a non-cyclic compound and subsequent cyclization, the reaction sequence being carried out in the presence of an anionic surfactant.

3 Claims, No Drawings

PREPARATION OF PHENYLOXADIAZOLYLANILINES

The present invention relates to a novel process for preparing phenyloxadiazolylanilines by reaction of a benzonitrile in an aqueous reaction medium first with hydroxylamine or an acid addition salt thereof, to give a benzamideoxime, and with an isatoic anhydride, to give a non-cyclic compound, and subsequent cyclization, the reaction sequence being carried out in the presence of an anionic surfactant.

DE-A-2 457 687 discloses the preparation of 2-(3-phenyl-1,2,4-oxadiazol-5-yl)aniline. According to the method described therein, benzonitrile is first reacted with hydroxylammonium sulfate in a mixture of water and isobutanol and in the presence of sodium carbonate to give benzamideoxime. After the aqueous phase has been separated off, the benzamideoxime can then be further reacted in the isobutanol phase with isatoic anhydride in the presence of finely pulverulent sodium methoxide to give the target product.

The phenyloxadiazolylaniline thus obtained serves as a diazo component for the pigments described in DE-A-2 457 687. The diazotization of the phenyloxadiazolylaniline with sodium nitrite in dilute hydrochloric acid does not go to completion, owing to the low solubility not only of the amine but also of its diazonium salt, and this impairs the application properties of the abovementioned pigments For this reason the diazotization of phenyloxadiazolylaniline must be carried out in a mixture of sulfuric acid and nitrosylsulfuric acid.

Even if the reaction of the benzamideoxime to give phenyloxadiazolylaniline is carried out not in isobutanol but a mixture of isobutanol and water and in the presence of sodium hydroxide, and the isobutanol is removed by means of steam distillation, the phenyloxadiazolylaniline obtained is likewise not completely diazotizable in dilute hydrochloric acid.

It is an object of the present invention to provide a new process whereby the preparation of phenyloxadiazolylanilines should be possible in a simple manner and in good yields and the target product produced thereby should also be readily diazotizable in dilute hydrochloric acid.

We have found that this object is achieved by preparing a phenyloxadiazolylaniline of formula I

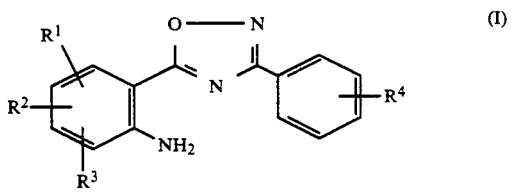

where
$R^1$ is hydrogen, halogen, $C_1$–$C_4$-alkyl, $C$–$C_4$-alkoxy, trifluoromethyl or nitro,
$R^2$ is hydrogen, halogen or nitro,
$R^3$ is hydrogen or halogen and
$R^4$ is hydrogen, halogen, $C_1$–$C_4$-alkyl, $C_1$–$C_4$alkoxy or nitro,
by reacting a benzonitrile of the formula II

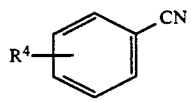

where $R^4$ is as defined above, in an aqueous reaction medium first with hydroxylamine, or an acid addition salt thereof, to give a benzamideoxime of the formula III

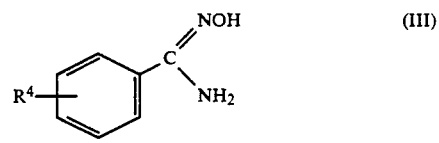

where $R^4$ is as defined above, and then with an isatoic anhydride of the formula IV

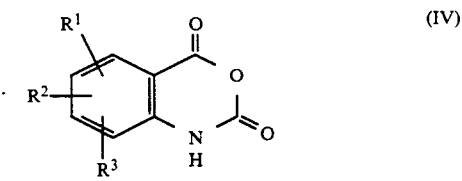

where $R^1$, $R^2$ and $R^3$ are each as defined above, to give a non-cyclic compound of the formula V

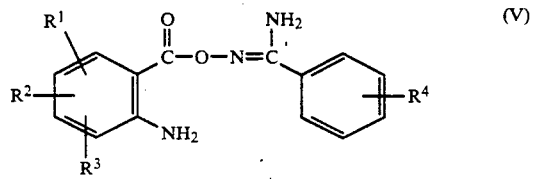

where $R^1$, $R^2$, $R^3$ and $R^4$ are each as defined above, and then cyclizing, which comprises carrying out the reaction sequence in the presence of an anionic surfactant.

All the alkyl groups appearing in the abovementioned formula I can be not only straight-chain but also branched $R^1$, $R^2$, $R^3$ and $R^4$ are each for example fluorine, chlorine or bromine $R^1$ and $R^4$ are each further for example methyl, ethyl, propyl, isopropyl, butyl, isobutyl, sec-butyl, tert-butyl, methoxy, ethoxy, propoxy, isopropoxy, butoxy, isobutoxy or sec-butoxy.

In the process according to the present invention, the benzonitrile II is reacted with hydroxylamine or an acid addition salt thereof. Acid addition salts of hydroxylamine are, for example, hydroxylammonium chloride, hydroxylammonium bromide and hydroxylammonium sulfate.

Preference is given to using an acid addition salt, of which hydroxylammonium sulfate is particularly preferred.

The anionic surfactants which find application in the process according to the present invention are substances known per se as described for example in Ullmanns Encyklopädie der Technischen Chemie, 4th edition, volume 22, pages 468–488.

Examples are carboxylates, such as carboxymethylated ethoxylates or derivatives of amino acids, sulfonates, such as alkylbenzenesulfonates, alkylnaphthalenesulfonates, alkanesulfonates, olefinsulfonates, sulfo(fatty acid) esters, sulfo(fatty acid) amides, sulfosuccinic esters, alkoxyalkanesulfonates, acyloxyalkanesulfonates, acylaminoalkanesulfonates, sulfates, such as alkyl sulfates or ether sulfates phosphonates and phosphates.

Preference is given to using sulfonate-based anionic surfactants in the process according to the present invention. The use of sulfo(fatty acid) esters and amides is particularly preferred.

In general, the anionic surfactant is used in an amount of from 3 to 20% by weight, preferably from 5 to 10% by weight, each percentage being based on the weight of benzonitrile II.

The novel process is carried out in an aqueous reaction medium. Preferably, the reaction is carried out in water which is essentially free of organic solvents It is of course also possible to carry out the reaction in a reaction medium which, although consisting predominantly of water, still contains a small amount (for example up to about 10% by weight based on the weight of the water present) of organic solvent, for example an alcohol, such as methanol, ethanol, propanol, isopropanol, butanol and isobutanol.

The process according to the present invention is in general carried out by initially dispersing the benzonitrile of the formula II together with the anionic surfactant in the aqueous reaction medium at 10–40° C. for 1–2 hours. This is followed by the addition of the hydroxylamine or an acid addition salt thereof and a base (eg. sodium carbonate, potassium carbonate or magnesium carbonate), and the reaction mixture is heated at 85–100° C. for 3–5 hours.

The reaction mixture, which now contains the benzamideoxime of the formula III, is then cooled back to 55–65° C. and the isatoic anhydride of the formula IV is added a little at a time to form initially the non-cyclic compound V.

A strong base (eg. sodium hydroxide, potassium hydroxide or aqueous solutions thereof) is then added to cyclize the non-cyclic compound V at 90–100° C. and pH 10–11 to the oxadiazole The target product is then filtered off with suction, washed with water and dried.

The molar ratio of benzonitrile II : hydroxylamine isatoic anhydride III is in general from 0.9:1:0.8 to 1:1:1.2.

The amount of base required for preparing the benzamideoxime III is in general dependent on the nature of the hydroxylammonium salt used, and is for example about 1.0–1.1 equivalents per equivalent of hydroxylammonium sulfate.

Preferably, the process according to the present invention is carried out with a benzonitrile of the formula II where $R^4$ is hydrogen and with an isatoic anhydride of the formula IV where $R^1$ is hydrogen, chlorine or bromine, $R^2$ is hydrogen, chlorine or bromine and $R^3$ is hydrogen, thus arriving at phenyloxadiazolylanilines of the formula I where $R^1$ is hydrogen, chlorine or bromine, $R^2$ is hydrogen, chlorine or bromine and $R^3$ and $R^4$ are each hydrogen.

In some cases it can be advantageous to isolate the non-cyclic compound V (for example by filtering off with suction or siphoning off the mother liquor by means of a probe) and then to disperse it for the cyclization reaction in aqueous potassium, or preferably sodium, hydroxide solution.

An advantage of the process according to the present invention is that it can be carried out virtually without organic solvent, hence obviating the need for the costly recovery of alcohols practised in the prior art process.

The novel process produces the phenyloxadiazolylaniline I in the form of finely divided crystals. They can then be completely diazotized with sodium nitrite in dilute hydrochloric acid. This is of particular advantage, since the large amount of acid obtained in the diazotization in sulfuric acid/nitrosylsulfuric acid is avoided.

Coupling the diazonium compound which has been prepared in dilute hydrochloric acid with a suitable coupling component (eg. 3-cyano-6-hydroxy-4-methylpyrid-2-one) produces, in high yield, pigments which have the same application properties as those prepared by the process described in DE-A-2 457 687.

Another favorable aspect is that it is now possible to render such a pigment suspension alkaline with sodium hydroxide solution and to coat the pigment in a conventional manner with dispersants, for example natural or synthetic resins, in a one-pot process. This is because in the prior art process described the pigment must first be isolated and re-dispersed in water before being coated with a resin, since otherwise the large amount of salt produced on neutralization does not permit thorough mixing of the reaction batch.

The following Examples further illustrate the invention:

EXAMPLE 1

120 g of benzonitrile and 7.5 g of an anionic 20 surfactant (sodium salt of sulfonated N,N-dibutyloleamide) were dispersed in 375 ml of water at room temperature in the course of an hour. 98 g of hydroxylammonium sulfate were added, followed by 67.5 g of sodium carbonate added a little at a time. The mixture was heated to 90° C. and stirred at that temperature for five hours. It was then cooled back to 60° C., and 190 g of isatoic anhydride were added a little at a time at that temperature. The reaction mixture, which contains the non-cyclic compound, was heated back to 90° C., brought to pH 10.5-11.0 with 50% strength by weight sodium hydroxide solution, and stirred at that temperature for one hour. The precipitate was filtered off with suction, washed with water and dried, comprising 222 g of 2-(3-phenyl-1,2,4-oxadiazol-5-yl)aniline in a finely divided crystal form.

EXAMPLE 2

Example 1 was repeated, except that the addition of 190 g of isatoic anhydride was followed by heating to 90° C. and stirring at that temperature for one hour. The reaction mixture was then diluted with cold water to a volume of 3 l, the product was allowed to settle, and the mother liquor was siphoned off with a probe. This procedure was repeated twice. After renewed addition of water, the batch was heated with stirring to 90° C. and adjusted to a pH 10.5-11 with 50% strength by weight sodium hydroxide solution. After two hours' stirring at 90° C., the target product was filtered off with suction, washed and dried, leaving 223 g of 2-(3-phenyl-1,2,4-oxadiazol-5-yl)aniline in a finely divided crystal form.

EXAMPLE 3

Example 1 was repeated, except that the noncyclic compound was filtered off with suction, washed and re-dispersed in 2000 ml of water. The dispersion was heated to 90° C., adjusted to pH 10.5-11 with 50% strength by weight sodium hydroxide solution and subsequently stirred at that temperature for two hours. Filtering off with suction, washing and drying left 214 g of 2-(3-20 phenyl-1,2,4-oxadiazol-5-yl)aniline in a finely divided crystal form.

EXAMPLE 4

48 g of benzonitrile and 3 g of an anionic surfactant (sodium salt of sulfonated N,N-dibutyloleamide) were dispersed in 150 ml of water at room temperature in the course of an hour. 39.2 g of hydroxylammonium sulfate were added, followed by 27 g of sodium carbonate added a little at a time. The reaction was heated to 90° C., stirred at that temperature for five hours and then cooled back to 60° C. 112 g of 5-bromoisatoic anhydride was then added, and the mixture was again heated to 90° C. After two hours' stirring at that temperature, the product was filtered off with suction, washed and redispersed in 1200 ml of water. The pH was adjusted to 10.5-11.0 with 50% strength by weight sodium hydroxide solution, the mixture was stirred at that temperature for one hour and then filtered with suction. The filter residue was washed with water and dried, leaving 110 g of 4-bromo-2-(3-phenyl-1,2,4-oxadiazol-5-yl)aniline in a very finely divided crystal form.

EXAMPLE 5 (COMPARISON)

To a solution of 151 g of sodium carbonate in 650 ml of water at room temperature were added in succession 650 ml of isobutanol, 268 g of benzonitrile and, a little at a time, 220 g of hydroxylammonium sulfate The mixture was then heated to 90° C. and stirred at that temperature for five hours It was then cooled back to 30-40° C. and 392 g of isatoic anhydride were added a little at a time at that temperature. The reaction mixture was then heated back up to 80° C. and 100 g of 50% strength by weight sodium hydroxide solution were added dropwise. The isobutanol was then distilled off quantitatively by introducing steam, and the coarsely crystalline residue was filtered off with suction, washed with water and dried, leaving 470 g of 2-(3-phenyl-1,2,4-oxadiazol-5-yl)aniline in a coarsely crystalline form.

EXAMPLE 6 (USE AS DIAZO COMPONENT)

59 g (calculated dry) of 2-(3-phenyl-1,2,4-oxadiazol-5-yl)aniline (of Example 3) were dispersed as a water-moist press cake in 700 ml of water and 80 ml of concentrated hydrochloric acid at 90° C. The dispersion was cooled down with stirring to room temperature and diazotized portionwise with 70 g of 23% strength by weight sodium nitrite solution while the temperature was maintained below 10° C. with ice. After the excess nitrite had been destroyed with amidosulfuric acid, 36.5 g of 3-cyano-6-hydroxy-4-methylpyrid-2-one in 400 ml of water and 15 g of 50% strength by weight sodium hydroxide solution were added. The mixture was heated to 40° C., stirred at that temperature for one hour and filtered with suction. The filter residue was washed with water and dried, leaving 95.2 g of a yellow pigment which has the same application properties in printing inks as a pigment prepared with the oxadiazolylaniline of Comparative Example No. 5 (replicating the method described in Example 1 of DE-A-2 452 687) and conditioned at 40° C.

We claim:

1. A process for preparing a phenyloxadiazolylaniline of formula I

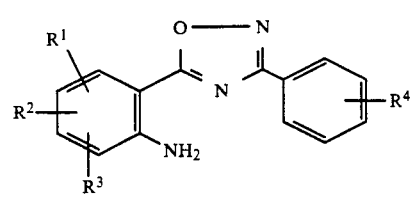

where $R^1$ is hydrogen, halogen, $C_1$-$C_4$-alkyl, $C_1$-$C_4$-alkoxy, trifluoromethyl or nitro,
$R^2$ is hydrogen, halogen or nitro,
$R^3$ is hydrogen, halogen and
$R^4$ is hydrogen, halogen, $C_1$-$C_4$-alkyl, $C_1$-$C_4$-alkoxy, or nitro,
by reacting a benzonitrile of the formula II

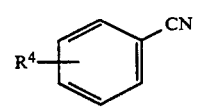

where $R^4$ is as defined above, in an aqueous reaction medium first with hydroxylamine, or an acid addition salt thereof, to give a benzamideoxime of the formula III

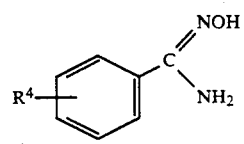

where $R^4$ is as defined above, and then with an isatoic anhydride of the formula IV

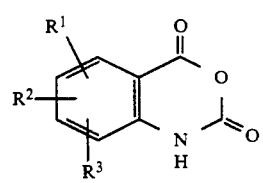

where $R^1$, $R^2$ and $R^3$ are each as defined above, to give a noncyclic compound of the formula V

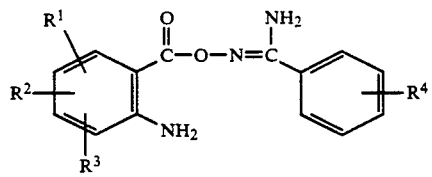

where $R^1$, $R^2$, $R^3$ and $R^4$ are each as defined above, and then cyclizing, which comprises carrying out the reaction sequence in the presence of an anionic surfactant.

2. A process as claimed in claim 1, wherein the reaction is carried out with a benzonitrile of the formula II where $R^4$ is hydrogen and with an isatoic anhydride of the formula IV where $R^1$ is hydrogen, chlorine or bromine, $R^2$ is hydrogen, chlorine or bromine and $R^3$ is hydrogen.

3. A process as claimed in claim 1, wherein the reaction is carried out in water which is essentially free of organic solvent.

* * * * *